United States Patent [19]

Takahashi et al.

[11] Patent Number: 4,562,281
[45] Date of Patent: Dec. 31, 1985

[54] PRODUCTION OF BISPHENOL DERIVATIVES

[75] Inventors: Yukoh Takahashi, Toyonaka; Yutaka Terada, Nishinomiya; Shinichi Yachigo, Toyonaka; Tamaki Ishii, Suita, all of Japan

[73] Assignee: Sumitomo Chemical Company, Limited, Osaka, Japan

[21] Appl. No.: 561,207

[22] Filed: Dec. 14, 1983

[51] Int. Cl.[4] .............................................. C07C 67/08
[52] U.S. Cl. .................... 560/104; 560/108; 560/140
[58] Field of Search ............... 560/104, 108, 140, 144

[56] References Cited

U.S. PATENT DOCUMENTS

| | | | |
|---|---|---|---|
| 3,984,372 | 10/1976 | Cottman | 528/125 |
| 4,065,489 | 12/1977 | Steinstrasser et al. | 560/108 |
| 4,168,387 | 9/1979 | Cottman | 560/144 |
| 4,274,998 | 6/1981 | Yamashita et al. | 560/108 |
| 4,365,032 | 12/1982 | Yosizato et al. | 560/140 |

FOREIGN PATENT DOCUMENTS

| | | | |
|---|---|---|---|
| 0079806 | 5/1983 | European Pat. Off. | |
| 0024080 | 12/1961 | Japan | 560/108 |
| 0059963 | 4/1983 | Japan | 560/140 |

OTHER PUBLICATIONS

Weygand, *Preparative Organic Chemistry*, p. 369, John Wiley and Sons, New York, 1972.
*Journal of the American Chemical Society*, vol. 77, pp. 6214–6215, 1955; Brewster et al.
J. Am. Chem. Soc., 60 1325 (1938), pp. 1325–1328.

*Primary Examiner*—Natalie Trousof
*Assistant Examiner*—Patricia M. Scott
*Attorney, Agent, or Firm*—Wenderoth, Lind & Ponack

[57] ABSTRACT

Bisphenol derivatives of the formula (I),

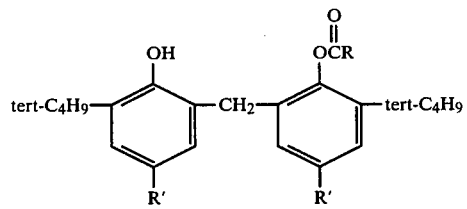

are produced by reacting a carboxylic acid, RCOOH (II), with a bisphenol of the formula (III),

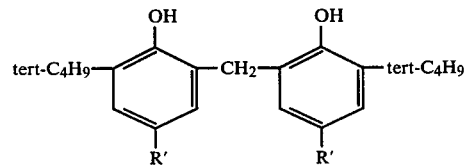

adding a halogenating agent in the presence of a dehydrohalogenating agent. The product bisphenol derivatives are useful as antioxidants.

12 Claims, No Drawings

PRODUCTION OF BISPHENOL DERIVATIVES

The present invention relates to a method for producing bisphenol derivatives represented by the formula (I),

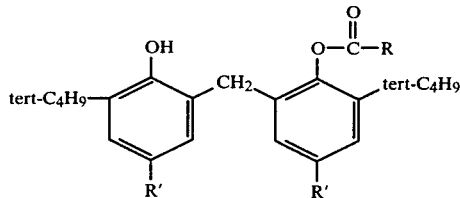

wherein R represents an alkyl group having 1 to 3 carbon atoms, alkenyl group having 2 to 4 carbon atoms, phenyl group or 2-phenylethenyl group, and R' represents an alkyl group having 1 to 4 carbon atoms.

A bisphenol derivative represented by the formula (I) is a useful compound as an antioxidant. As a method for producing it, there is known a method in which a carboxylic acid is converted to its acid halide using a halogenating agent such as chlorinating agents (e.g. thionyl chloride, phosphorus trichloride, phosphorus pentachloride) or brominating agents (e.g. phosphorus tribromide), and the acid halide is then reacted with bisphenols in the presence of a dehydrohalogenating agent (U.S. Pat. No. 3,984,372). When the method like this is used, however, it was not avoidable that the reaction is necessarily carried out in two steps, and because of this, the yield of the bisphenol derivative based on the carboxylic acid lowers.

Besides, this two-step reaction makes it inevitable to handle an acid halide, which is a strongly irritative substance to eyes, skins, mucous membranes, etc., as an intermediate, which becomes a problem also in terms of working environment. There was a demand, therefore, for the development of a method for producing bisphenol derivatives in which the acid halide is not handled.

In view of the present situation like this, the present inventors extensively studied a method for producing bisphenol derivatives represented by the formula (I) which not only causes no problem in working environment but also gives a good overall yield of said bisphenol derivatives from, of course, bisphenols and also carboxylic acids. As a result, the present inventors found a novel method in which the objective compound is obtained in one step as well as in good yields without handling the strongly irritative acid halide, and thus attained to the present invention.

According to the present invention, there is provided a method for producing bisphenol derivatives represented by the foregoing formula (I) characterized in that a carboxylic acid represented by the formula (II), $$R-\overset{O}{\underset{\|}{C}}-OH \quad (II)$$

wherein R has the same meaning as above, is reacted with bisphenols represented by the formula (III),

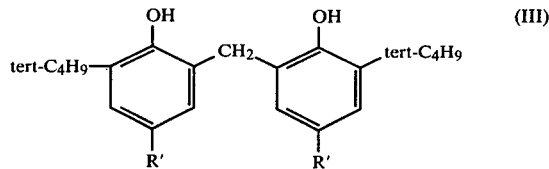

wherein R' has the same meaning as above, using a halogenating agent in the presence of a dehydrohalogenating agent.

In the present invention, specific examples of the carboxylic acid represented by the formula (II) include for example acetic acid, propionic acid, butyric acid, acrylic acid, methacrylic acid, crotonic acid, 3-butenoic acid, benzoic acid, cinnamic acid and the like. Specific examples of the bisphenols represented by the formula (III) include for example 2,2'-methylenebis(6-tert-butyl-4-methylphenol), 2,2'-methylenebis(6-tert-butyl-4-ethylphenol), 2,2'-methylenebis(6-tert-butyl-4-propylphenol), 2,2'-methylenebis(6-tert-butyl-4-n-butylphenol), 2,2'-methylenebis(6-tert-butyl-4-sec-butylphenol), and 2,2'-methylenebis(4,6-di-tert-butylphenol).

Specific examples of the dehydrohalogenating agent include for example tertiary amines such as triethylamine, dimethylaniline, N,N-dimethylbenzylamine, tetramethylurea, etc., and pyridine derivatives such as pyridine, 4-(N,N-dimethylamino)pyridine, etc.

As the halogenating agent, there are given for example phosphorus oxychloride, phosphorus oxybromide, o-toluenesulfonyl chloride, p-toluenesulfonyl chloride and the like.

The reaction of the present invention is generally carried out in the presence of a solvent. As the solvent, there are given for example aliphatic hydrocarbons (e.g. n-hexane, n-heptane), alicyclic ones (e.g. cyclohexane), aromatic ones (e.g. benzene, toluene, xylene), esters (e.g. ethyl acetate, butyl acetate), ethers (e.g. diethyl ether, tetrahydrofuran, ethylene glycol dimethyl ether), halogenated hydrocarbons (e.g. dichloromethane, chloroform, carbon tetrachloride, 1,2-dichloroethane), and dehydrohalogenating agents, which are liquid at room temperature, of those given above.

In this reaction, the molar ratio of carboxylic acid to bisphenol is generally 0.7–1.5:1, more preferably 0.9–1.2:1.

The amount of the halogenating agent used is in a range of 0.5 to 1.0 mole, preferably 0.6 to 0.9 mole, more preferably 0.65 to 0.8 mole based on 1 mole of the carboxylic acid for phosphorus oxychloride and phosphorus oxybromide, and it is in a range of 0.8 to 1.6 moles, preferably 0.9 to 1.2 moles based on 1 mole of the same for o- or p-toluenesulfonyl chloride.

The amount of the dehydrohalogenating agent used depends upon the kind of the halogenating agent. When the halogenating agent is phosphorus oxychloride or phosphorus oxybromide, said amount is in a range of 2.7 to 3.6 equivalents, preferably 2.9 to 3.2 equivalents based on 1 mole of the chlorinating agent. When the halogenating agent is o- or p-toluenesulfonyl chloride, said amount is in a range of 0.8 to 2.4 equivalents, preferably 0.9 to 2.2 equivalents based on 1 mole of the halogenating agent. An expression "equivalent" was used here for the reason that, of the dehydrohalogenating agents given above, some agents, for example tetramethylurea, will catch two hydrogen halide molecules per one molecule of them.

The reaction temperature is in a range of −20° C. to 150° C., preferably 0° C. to 120° C., more preferably 20° C. to 100° C.

After completion of the reaction, the objective product can be separated from the reaction solution by various methods as follows: After separating the acid salt of the dehydrohalogenating agent by filtration in advance or without separating it, the reaction solution is neutralized as need arises and washed with water, and the solvent is removed by evaporation from the organic layer; or water is added to the reaction solution which is then cooled, and the deposited crystal is separated. The objective product obtained may further be purified by the well-known methods such as recrystallization, washing with solvents, and the like.

As described above, according to the present invention, the bisphenol derivative represented by the formula (I) can be produced in one step, in good yields and easily in industry from the carboxylic acids without handling a strongly irritative acid halide.

The present invention will be illustrated hereinafter with reference to the following examples.

EXAMPLE 1

To a 2-liter four-necked flask equipped with a thermometer, stirring apparatus, condenser and dropping funnel were added 340.51 g (1.0 mole) of 2,2'-methylenebis(6-tert-butyl-4-methylphenol), 72.06 g (1.0 mole) of acrylic acid, 500 g of toluene and 209.47 g (2.07 moles) of triethylamine. After replacing the air in the container with nitrogen, 105.8 g (0.69 mole) of phosphorus oxychloride was added dropwise with stirring. After completion of the dropwise addition, the reaction solution was kept at 80° C. for 1 hour. Thereafter, the organic layer was washed with water until it became neutral, and toluene was removed under reduced pressure. The residue was then recrystallized from n-hexane to obtain 374.8 g of a white crystalline 2,2'-methylenebis(6-tert-butyl-4-methylphenol) monoacrylate having a melting point of 132° to 134° C. Yield, 95%.

EXAMPLE 2

To the same flask as used in Example 1 were added 340.51 g (1.0 mole) of 2,2'-methylenebis(6-tert-butyl-4-methylphenol), 72.06 g (1.0 mole) of acrylic acid, 400 g of n-heptane and 212.5 g (2.10 moles) of triethylamine. After replacing the air in the container with nitrogen, 200.7 g (0.70 mole) of phosphorus oxybromide was added dropwise with stirring. After completion of the dropwise addition, the reaction solution was kept at 80° C. for 1 hour. Thereafter, 500 g of water was added, and after cooling to room temperature, the deposited product was filtered off. The product obtained was washed with water until the washing became neutral to obtain 379.6 g of 2,2'-methylenebis(6-tert-butyl-4-methylphenol) monoacrylate as a white crystal. Melting point, 132°–134° C. Yield, 96%.

EXAMPLE 3

To the same flask as used in Example 1 were added 340.51 g (1.0 mole) of 2,2'-methylenebis(6-tert-butyl-4-methylphenol), 86.41 g (1.0 mole) of 98.5% methacrylic acid, 500 g of toluene and 242.86 g (2.4 moles) of triethylamine. After replacing the air in the container with nitrogen, 229.14 g (1.2 moles) of o-toluenesulfonyl chloride was added dropwise with stirring. After completion of the dropwise addition, the reaction solution was kept at 90° C. for 1 hour. Thereafter, the organic layer was washed with water until it became neutral, and toluene was removed under reduced pressure. The residue was recrystallized from n-hexane to obtain 384.1 g of a white crystalline 2,2'-methylenebis(6-tert-butyl-4-methylphenol) monomethacrylate having a melting point of 144° to 146° C. Yield, 94%.

EXAMPLE 4

To the same flask as used in Example 1 were added 340.51 g (1.0 mole) of 2,2'-methylenebis(6-tert-butyl-4-methylphenol), 74.08 g (1.0 mole) of propionic acid, 500 g of toluene and 191.42 g (2.42 moles) of pyridine. After replacing the air in the container with nitrogen, 210.05 g (1.1 moles) of o-toluenesulfonyl chloride was added dropwise with stirring. After completion of the dropwise addition, the reaction solution was kept at 100° C. for 1 hour and then aftertreated in the same manner as in Example 2 to obtain 384.7 g of a white crystalline 2,2'-methylenebis(6-tert-butyl-4-methylphenol) monopropionate having a melting point of 108° to 110° C. Yield, 97%.

EXAMPLE 5

To the same flask as used in Example 1 were added 340.51 g (1.0 mole) of 2,2'-methylenebis(6-tert-butyl-4-methylphenol), 122.12 g (1.0 mole) of benzoic acid, 500 g of toluene and 242.86 g (2.4 moles) of triethylamine. After replacing the air in the container with nitrogen, 229.15 g (1.2 moles) of o-toluenesulfonyl chloride was added dropwise with stirring. After completion of the dropwise addition, temperature maintenance and aftertreatment were carried out in the same manner as in Example 3 to obtain 426.83 g of a white crystalline 2,2'-methylenebis(6-tert-butyl-4-methylphenol) monobenzoate having a melting point of 149° to 151° C. Yield, 96%.

Example 6

To a 2-liter four-necked flask equipped with a thermometer, stirring apparatus, condenser and feed inlet were added 340.51 g (1.0 mole) of 2,2'-methylenebis(6-tert-butyl-4-methylphenol), 60.05 g (1.0 mole) of acetic acid and 800 g of triethylamine. After replacing the air in the container with nitrogen, 305.52 g (1.6 moles) of p-toluenesulfonyl chloride was added little by little with stirring. After completion of the addition, the reaction solution was kept at 60° C. for 1 hour with stirring, and then triethylamine hydrochloride formed was filtered off at room temperature. The triethylamine hydrochloride was further washed with toluene, and the filtrate and toluene washing were mixed and washed with water until the mixture became neutral. Thereafter, the solvent was removed under reduced pressure, and the residue was recrystallized from n-hexane to obtain 344.3 g of a white crystalline 2,2'-methylenebis(6-tert-butyl-4-methylphenol) monoacetate having a melting point of 98° to 104° C. Yield, 90%.

EXAMPLE 7

To the same flask as used in Example 6 were added 340.51 g (1.0 mole) of 2,2'-methylenebis(6-tert-butyl-4-methylphenol), 151.18 g (1.0 mole) of cinnamic acid, 500 g of toluene and 118.65 g (1.5 moles) of pyridine. After replacing the air in the container with nitrogen, 286.43 g (1.5 moles) of p-toluenesulfonyl chloride was added little by little with stirring. After completion of the addition, temperature maintenance and after-treatment were carried out in the same manner as in Example 6, and the residue was recrytallized from toluene to obtain 404.8 g of a white crystalline 2,2'-methylenebis(6-tert-butyl-4-methylphenol) monocinnamoate having a melting point of 164° to 169° C. Yield, 86%.

COMPARATIVE EXAMPLE 1

To a 500-ml four-necked flask equipped with a thermometer, stirring apparatus, condenser and dropping funnel were added 144.1 g (2.0 moles) of 99.8% acrylic acid, 2.0 g (0.03 mole) of N,N-dimethylformamide and 1.44 g (0.01 mole) of hydroquinone, and 238.0 g (2.0 moles) of thionyl chloride was added dropwise with stirring while maintaining the inner temperature at 50° C. After completion of the dropwise addition, temperature maintenance was carried out for 30 minutes, 0.14 g (0.0013 mole) of cuprous chloride was then added and the product was distilled under normal pressure to collect a fraction between 71° C. and 85° C. Thus, 70.60 g of acryloyl chloride was obtained. Yield, 39%.

To a 500-ml four-necked flask equipped with a thermometer, stirring apparatus, condenser and dropping funnel were added 82.0 g (0.241 mole) of 2,2'-methylenebis(6-tert-butyl-4-methylphenol), 200 g of toluene and 23.9 g (0.290 mole) of triethylamine. After replacing the air in the container with nitrogen, 25 g (0.276 mole) of acryloyl chloride was added dropwise with stirring. After completion of the dropwise addition, stirring was continued for 1 hour, excess triethylamine was neutralized with a dilute hydrochloric acid and the formed triethylamine hydrochloride was then removed by washing with water. Toluene was then removed by evaporation from the toluene layer after completion of the washing, and the residue obtained was recrystallized from 20 g of n-hexane to obtain 90.0 g of 2,2'-methylenebis(6-tert-butyl-4-methylphenol) monoacrylate as a white crystal. Melting point, 132°-134° C. Yield, 95%.

The yield of the product based on acrylic acid was 37.1%.

COMPARATIVE EXAMPLE 2

To a 2-liter four-necked flask equipped with a thermometer, stirring apparatus, condenser and dropping funnel were added 340.51 g (1.00 mole) of 2,2'-methylenebis(6-tert-butyl-4-methylphenol), 500 g of toluene and 113.41 g (1.12 moles) of triethylamine. After replacing the air in the container with nitrogen, 93.28 g (1.01 mole) of acryloyl chloride was added dropwise with stirring.

After completion of the dropwise addition, stirring was continued for 1 hour, excess triethylamine was converted to its hydrochloride with a dilute hydrochloric acid, and the formed triethylamine hydrochloride was removed by washing with water. After washing with water, toluene was removed by evaporation from the toluene layer, and the residue obtained was recrystallized from 425 g of n-hexane to obtain 286.96 g of 2,2'-methylenebis(6-tert-butyl-4-methylphenol) monoacrylate as a white crystal. Melting point, 132°-134° C. Yield, 72.7%.

The yield of the product based on acrylic acid was 28.3%.

COMPARATIVE EXAMPLE 3

Propionyl chloride was obtained from propionic acid and benzoyl chloride according to the method described in J.A.C.S., 60, 1325 (1938). Yield, 89%. Boiling point, 77°-78.5° C.

To a 300-ml four-necked flask equipped with a thermometer, stirring apparatus and condenser were added 34.51 g (0.10 mole) of 2,2'-methylenebis(6-tert-butyl-4-methylphenol), 50 g of toluene and 11.13 g (0.11 mole) of triethylamine. After replacing the air in the container with nitrogen, 10.20 g (0.11 mole) of propionyl chloride was added dropwise. After completion of the dropwise addition, after-treatment was carried out in the same manner as in Comparative example 1 to obtain 35.0 g of 2,2'-methylenebis(6-tert-butyl-4-methylphenol) monopropionate as a white crystal. Melting point, 108°-111° C. Yield, 88.4%.

The yield of the product based on propionic acid was 78%.

What is claimed is:

1. A method for producing bisphenol derivatives represented by the formula (I),

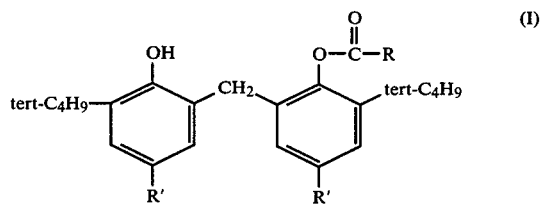

wherein R represents an alkyl group having 1 to 3 carbon atoms, alkenyl group having 2 to 4 carbon atoms, phenyl group or 2-phenyl-ethenyl group, and R' represents an alkyl group having 1 to 4 carbon atoms, characterized in that a carboxylic acid represented by the formula (II),

wherein R has the same meaning as above, is reacted at a temperature of −20° C. to 150° C. with a bisphenol represented by the formula (III),

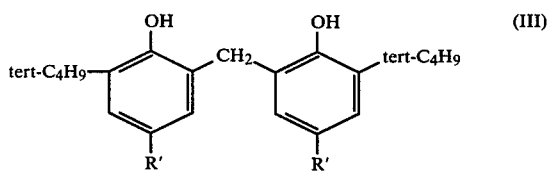

wherein R' has the same meaning as above, adding a halogenating agent selected from the group consisting of phosphoryl chlorides, phosphoryl bromides and toluenesulfonyl chloride to the reaction mixture, wherein the reaction is carried out in the presence of a dehydrohalogenating agent selected from the group consisting of tertiary amines and pyridine derivatives.

2. A method as described in claim 1, wherein the halogenating agent is phosphorus oxychloride or phosphorus oxybromide.

3. A method as described in claim 1, wherein the halogenating agent is o-toluenesulfonyl chloride or p-toluenesulfonyl chloride.

4. A method as described in claim 1, wherein the carboxylic acid is one member selected from the group consisting of acetic acid, propionic acid, butyric acid, acrylic acid, methacrylic acid, crotonic acid, 3-butenoic acid, benzoic acid and cinnamic acid.

5. A method as described in claim 1, wherein the bisphenol is one member selected from the group consisting of 2,2'-methylenebis(6-tert-butyl-4-methylphenol), 2,2'-methylenebis(6-tert-butyl-4-ethylphenol), 2,2'-methylenebis(6-tert-butyl-4-propylphenol), 2,2'-methylenebis(6-tert-butyl-4-n-butylphenol), 2,2'-methylenebis(6-tert-butyl-4-sec-butylphenol) and 2,2'-methylenebis(4,6-di-tert-butylphenol).

6. A method as described in claim 1, wherein the tertiary amine is one member selected from the group consisting of triethylamine, dimethylaniline, N,N-dimethylbenzylamine and tetramethylurea.

7. A method as described in claim 1, wherein the pyridine derivative is one member selected from the group consisting of pyridine and 4-(N,N-dimethylamino)pyridine.

8. A method as described in claim 1, wherein the molar ratio of carboxylic acid to bisphenol is 0.7–1.5:1.

9. A method as described in claim 2, wherein the amount of phosphorus oxychloride or phosphorus oxybromide used is 0.5 to 1.0 mole based on 1 mole of the carboxylic acid.

10. A method as described in claim 3, wherein the amount of o- or p-toluenesulfonyl chloride used is 0.8 to 1.6 moles based on 1 mole of the carboxylic acid.

11. A method as described in claim 2, wherein the amount of the dehydrohalogenating agent used is 2.7 to 3.6 equivalents based on 1 mole of the halogenating agent.

12. A method as described in claim 3, wherein the amount of the dehydrohalogenating agent used is 0.8 to 2.4 equivalents absed on 1 mole of the halogenating agent.

* * * * *